(12) United States Patent
Sawai et al.

(10) Patent No.: US 6,774,104 B1
(45) Date of Patent: Aug. 10, 2004

(54) STABILIZED PHARMACEUTICAL COMPOSITION IN LYOPHILIZED FORM

(75) Inventors: Seiji Sawai, Hyogo (JP); Akihiro Kasai, Nara (JP); Kazumi Otomo, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 193 days.

(21) Appl. No.: 09/786,125

(22) PCT Filed: Jun. 29, 2000

(86) PCT No.: PCT/JP00/04381

§ 371 (c)(1),
(2), (4) Date: Mar. 1, 2001

(87) PCT Pub. No.: WO01/02002

PCT Pub. Date: Jan. 11, 2001

(30) Foreign Application Priority Data

Jul. 1, 1999 (JP) .......................... 11/187713

(51) Int. Cl.[7] .......................... A61K 38/00; A61K 38/12
(52) U.S. Cl. ................. 514/9; 514/2; 514/9; 514/11; 514/15; 530/317; 530/323
(58) Field of Search ............... 530/317, 323; 514/9, 11, 15

(56) References Cited

U.S. PATENT DOCUMENTS

| | | | |
|---|---|---|---|
| 5,376,634 A | * | 12/1994 | Iwamoto et al. |
| 5,569,646 A | * | 10/1996 | Ohki et al. |
| 5,942,510 A | * | 8/1999 | Floyd et al. |
| 6,207,434 B1 | * | 3/2001 | Ueda et al. |
| 6,399,567 B1 | * | 6/2002 | Kanasaki et al. |

FOREIGN PATENT DOCUMENTS

| | | |
|---|---|---|
| JP | 3-193735 | 8/1991 |
| JP | 3-240727 | 10/1991 |
| JP | 6-51641 | 7/1994 |
| JP | 9-301997 | 11/1997 |
| JP | 10-507174 | 7/1998 |
| WO | WO 96/11210 | * 4/1996 |
| WO | WO 00/51564 | * 9/2000 |
| WO | WO 00/51567 | * 9/2000 |

* cited by examiner

Primary Examiner—Brenda Brumback
Assistant Examiner—Billy D. Chism
(74) Attorney, Agent, or Firm—Oblon, Spivak, McClelland, Maier & Neustadt, P.C.

(57) ABSTRACT

A stabilized pharmaceutical composition in lyophilized form comprising: a cyclic polypeptide compound represented by the general formula (I):

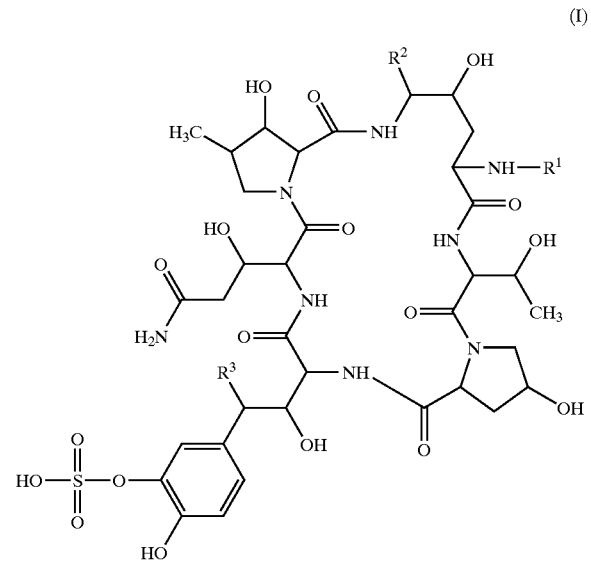

wherein $R^1$ is a hydrogen atom or an acyl group and $R^2$ and $R^3$ are, the same or different, a hydrogen atom or a hydroxyl group, or a salt thereof and the stabilizer.

19 Claims, No Drawings

STABILIZED PHARMACEUTICAL COMPOSITION IN LYOPHILIZED FORM

TECHNICAL FIELD

The present invention relates to a stabilized pharmaceutical composition in lyophilized form containing a cyclic polypeptide compound. More particularly, the present invention relates to a stabilized pharmaceutical composition in lyophilized form containing a cyclic polypeptide compound or its pharmaceutically acceptable salt and a stabilizer.

The cyclic polypeptide compound of the present invention is represented by the general formula (I):

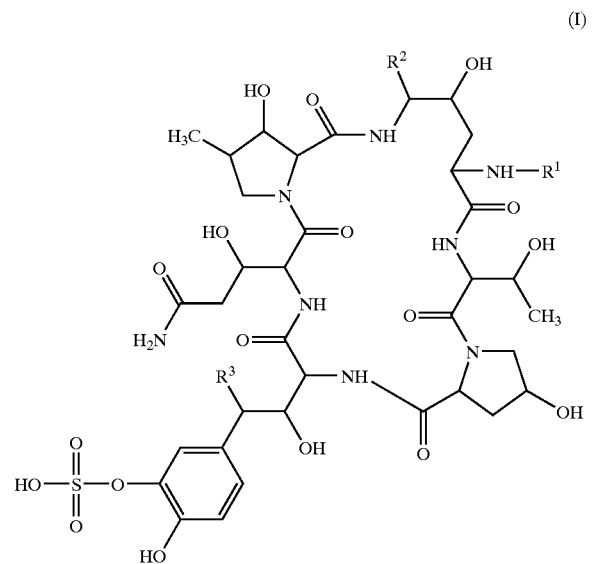

wherein $R^1$ is a hydrogen atom or an acyl group and $R^2$ and $R^3$ are, the same or different, a hydrogen atom or a hydroxyl group. The compound has an antimicrobial activity, particularly an antifungal activity and a β-1,3-glucan synthase inhibiting action, and is useful for preventing and treating various kinds of infectious diseases including Pneumocystis carinii infection, e.g., carinii pneumonia.

BACKGROUND ART

Among the cyclic polypeptide compounds represented by the above formula (I), a compound wherein $R^1$ is a hydrogen atom and $R^2$ and $R^3$ are hydroxyl groups and a compound wherein $R^1$, $R^2$ and $R^3$ are hydrogen atoms are obtained by a fermentation process disclosed by European Patent No. 0462531 and processes disclosed by WO97/32975 and by WO97/47738. A compound wherein $R^1$ is an acyl group and its production process are disclosed by U.S. Pat. Nos. 5,376,634 and 5,569,646 and WO96/11210 and WO99/40108.

The cyclic polypeptide compounds (I) and their salts are generally unstable to light, humidity, acids, heat and the like. Therefore, desired is development of pharmaceutical preparations in which the cyclic polypeptide compounds and their salts are stabilized.

DISCLOSURE OF INVENTION

The present invention provides a stabilized pharmaceutical composition in lyophilized form containing a cyclic polypeptide compound (I) or its pharmaceutically acceptable salt and a stabilizer.

The "acyl group" for $R^1$ in the formula (I) representing the cyclic polypeptide compound of the present invention is now explained. In the context of the present specification, "lower" means having one to six carbon atoms unless otherwise indicated.

As examples of the acyl group, may be mentioned aliphatic acyl groups, aromatic acyl groups, aromatic-aliphatic acyl groups and heterocyclic acyl groups derived from aliphatic, aromatic, aromatic-aliphatic and heterocyclic carboxylic acids.

Examples of the aliphatic acyl groups include lower or higher alkanoyl groups such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.; cycloalkanoyl groups such as cyclopentanoyl and cyclohexanoyl; lower alkoxycarbonyl groups such as methoxycarbonyl, ethoxycarbonyl, t-butoxycarbonyl, t-pentyloxycarbonyl, heptyloxycarbonyl, etc.; lower alkanesulfonyl groups such as methanesulfonyl, ethanesulfonyl, etc.; lower alkoxysulfonyl groups such as methoxysulfonyl, ethoxysulfonyl, etc.; and the like.

Examples of the aromatic acyl groups include aroyl groups such as benzoyl, toluoyl, naphthoyl and the like.

Examples of the aromatic-aliphatic acyl groups include
ar(lower)alkanoyl groups such as phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthylpropanoyl, naphthylbutanoyl, etc.) and the like;

ar(lower)alkenoyl groups such as phenyl($C_3$–$C_6$)alkenoyl (e.g., phenylpropenoyl, phenylbutenoyl, phenylmethacryloyl, phenylpentanoyl, phenylhexenoyl, etc.), naphthyl ($C_3$–$C_6$)alkenoyl (e.g., naphthylpropenoyl, naphthylbutenoyl, etc.) and the like;

ar(lower)alkoxycarbonyl groups such as phenyl($C_1$–$C_6$) alkoxycarbonyl (e.g., benzyloxycarbonyl, etc.), fluorenyl ($C_1$–$C_6$) alkoxycarbonyl (e.g., fluorenylmethoxycarbonyl, etc.) and the like;

aryloxycarbonyl groups such as phenoxycarbonyl, naphthoxycarbonyl, etc.;

aryloxy(lower)alkanoyl groups such as phenoxyacetyl, phenoxypropionyl, etc.;

arylcarbamoyl groups such as phenylcarbamoyl, etc.;

arylthiocarbamoyl groups such as phenylthiocarbamoyl, etc.;

arylglyoxyloyl groups such as phenylglyoxyloyl, naphthylglyoxyloyl, etc.;

arylsulfonyl groups which may be optionally substituted by a lower alkyl group such as phenylsulfonyl, p-tolylsulfonyl, etc.; and the like.

Examples of the heterocyclic acyl groups include heterocyclic
carbonyl groups such as thenoyl, furoyl, nicotinoyl, etc.;

heterocyclic(lower)alkanoyl groups such as heterocyclic acetyl, heterocyclic propanoyl, heterocyclic butanoyl, heterocyclic pentanoyl, heterocyclic hexanoyl, etc.;

heterocyclic(lower)alkenoyl groups such as heterocyclic propenoyl, heterocyclic butenoyl, heterocyclic pentenoyl, heterocyclic hexenoyl, etc.;

heterocyclic glyoxyloyl and the like.

The acyl group for $R^1$ may have one, or more suitable substituent(s). Among the above-mentioned examples for the acyl groups, an aroyl group which may have one or more suitable substituent(s) is particularly preferable.

Examples of suitable substituents in the acyl group include a heterocyclic group substituted by an aryl group having a lower alkoxy group, a heterocyclic group substituted by an aryl group having a lower alkoxy(lower)alkoxy group, a heterocyclic group substituted by an aryl group having a lower alkoxy(higher)alkoxy group, a heterocyclic group substituted by an aryl group having a cyclo(lower)alkyloxy group, a heterocyclic group substituted by an aryl group having a heterocyclic group, a heterocyclic group substituted by a cyclo(lower)alkyl group having a cyclo(lower)alkyl group, a heterocyclic group substituted by an aryl group having an aryl group substituted by a lower alkoxy(lower)alkoxy and a heterocyclic group substituted by an aryl group having a heterocyclic group substituted by a cyclo(lower)alkyl group.

Among these examples, preferred are an unsaturated 3- to 8-membered heteromonocyclic group containing one to two oxygen atom(s) and one to three nitrogen atom(s) and substituted by phenyl having $(C_4-C_6)$alkoxy, an unsaturated condensed heterocyclic group containing one to two sulfur atom(s) and one to three nitrogen atom(s) and substituted by phenyl having $(C_4-C_6)$alkoxy, an unsaturated 3- to 8-membered heteromonocyclic group containing one to two sulfur atom(s) and one to three nitrogen atom(s) and substituted by phenyl having $(C_1-C_4)$alkoxy$(C_4-C_6)$alkoxy, an unsaturated 3- to 8-membered heteromonocyclic group containing one to two sulfur atom(s) and one to three nitrogen atom(s) and substituted by phenyl having $(C_1-C_4)$alkoxy$(C_7-C_{14})$alkoxy, a saturated 3- to 8-membered heteromonocyclic group containing one to four nitrogen atom(s) and substituted by phenyl having $(C_1-C_4)$alkoxy$(C_7-C_{14})$alkoxy, an unsaturated condensed heterocyclic group containing one to two sulfur atom(s) and one to three nitrogen atom(s) and substituted by phenyl having cyclo$(C_4-C_6)$alkyloxy, an unsaturated condensed heterocyclic group containing one to two sulfur atom(s) and one to three nitrogen atom(s) and substituted by phenyl, a saturated 3- to 8-membered heteromonocyclic group containing one to two oxygen atom(s) and one to three nitrogen atom(s), a saturated 3- to 8-membered heteromonocyclic group having one to four nitrogen atom(s) and substituted by cyclo$(C_4-C_6)$alkyl having cyclo$(C_4-C_6)$alkyl, an unsaturated 3- to 8-membered heteromonocyclic group having one to two sulfur atom(s) and one to three nitrogen atom(s) and substituted by phenyl having phenyl substituted by $(C_1-C_4)$alkoxy$(C_1-C_4)$alkoxy, an unsaturated 3- to 8-membered heteromonocyclic group containing one to two sulfur atom(s) and one to three nitrogen atom(s) and substituted by phenyl having a saturated 3- to 8-membered heteromonocyclic group which contains one to four nitrogen atom(s) and is substituted by cyclo$(C_4-C_6)$alkyl and an unsaturated condensed heterocyclic group containing one to two sulfur atom(s) and one to three nitrogen atom(s) and substituted by phenyl having a saturated 3- to 8-membered heteromonocyclic group which contains one to four nitrogen atom(s) and has cyclo$(C_4-C_6)$alkyl.

Among these, particularly preferred are an isoxazolyl group substituted by phenyl having pentyloxy, an imidazothiadiazolyl group substituted by phenyl having pentyloxy, a thiadiazolyl group substituted by phenyl having methoxyhexyloxy, a thiadiazolyl group substituted by phenyl having methoxyoctyloxy, a thiadiazolyl group substituted by phenyl having methoxyheptyloxy, an imidazothiadiazolyl group substituted by phenyl having cyclohexyloxy, an imidazothiadiazolyl group substituted by phenyl having dimethylmorpholino, a piperazinyl group substituted by phenyl having methoxyheptyloxy, a piperazinyl group substituted by phenyl having methoxyoctyloxy, a piperazinyl group substituted by cyclohexyl having cyclohexyl, a thiadiazolyl group substituted by phenyl having phenyl substituted by methoxyethoxy, a thiadiazolyl group substituted by phenyl having phenyl substituted by methoxybutoxy, a thiadiazolyl group substituted by phenyl having phenyl substituted by ethoxypropoxy, an imidazothiadiazolyl group substituted by phenyl having piperazinyl substituted by cyclohexyl, an imidazothiadiazolyl group substituted by phenyl having piperazinyl substituted by cyclohexyl, and the like.

Accordingly, particularly suitable examples of the acyl group of $R^1$ may be a benzoyl group having isoxazolyl substituted by phenyl having pentyloxy, a benzoyl group having imidazothiadiazolyl substituted by phenyl having pentyloxy, a benzoyl group having thiadiazolyl substituted by phenyl having methoxyhexyloxy, a benzoyl group having thiadiazolyl substituted by phenyl having methoxyoctyloxy, a benzoyl group having thiadiazolyl substituted by phenyl having methoxyheptyloxy, a benzoyl group having imidazothiadiazolyl substituted by phenyl having cyclohexyloxy, a benzoyl group having imidazothiadiazolyl substituted by phenyl having dimethylmorpholino, a benzoyl group having piperazinyl substituted by phenyl having methoxyheptyloxy, a benzoyl group having piperazinyl substituted by phenyl having methoxyoctyloxy, a benzoyl group having piperazinyl substituted by cyclohexyl having cyclohexyl, a benzoyl group having thiadiazolyl substituted by phenyl having phenyl substituted by methoxyethoxy, a benzoyl group having thiadiazolyl substituted by phenyl having phenyl substituted by methoxybutoxy, a benzoyl group having thiadiazolyl substituted by phenyl having phenyl substituted by ethoxypropoxy, a benzoyl group having imidazothiadiazolyl substituted by phenyl having piperazinyl substituted by cyclohexyl, a benzoyl group having imidazothiadiazolyl substituted by phenyl having piperazinyl substituted by cyclohexyl, and the like.

Particularly preferable examples of the acyl groups of $R^1$ are represented by the formulas:

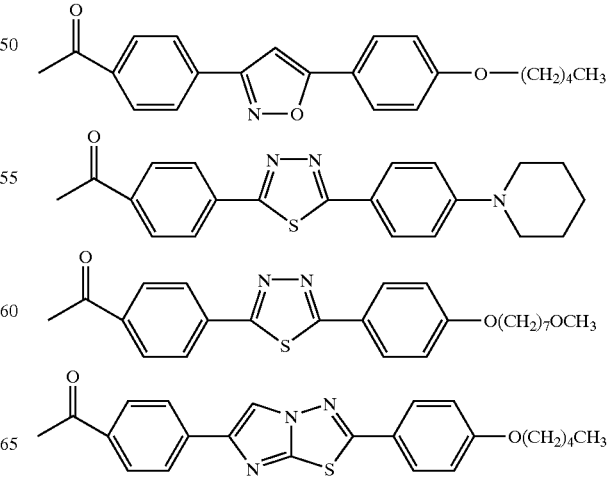

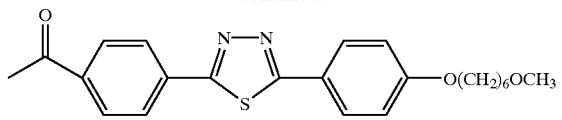

The cyclic polypeptide compounds (I) having the above-mentioned acyl groups may be prepared from a compound having a hydrogen atom as $R^1$ and hydroxyl groups as $R^2$ and $R^3$ or a compound having hydrogen atoms as $R^1$, $R^2$ and $R^3$ according to the U.S. Pat. Nos. 5,376,634 and 5,569,646 and WO96/11210 and WO99/40108.

Suitable salts of the cyclic polypeptide compounds (I) are soluble in water and pharmaceutically acceptable salts including salts with bases and acid addition salts. Such a salt may be prepared by treating the cyclic polypeptide compound (I) with an appropriate base or acid according to the conventional method.

As salts with bases, may be mentioned salts with inorganic bases such as alkali metal salts (e.g., sodium salts, potassium salts, etc.), alkaline earth metal salts (e.g., calcium salts, magnesium salts, etc.), ammonium salts and the like; salts with organic bases such as organic amine salts (e.g., triethylamine salts, diisopropylethylamine salts, pyridine salts, picoline salts, ethanolamine salts, triethanolamine salts, dicyclohexylamine salts, N,N'-dibenzylethylenediamine salts, etc.); and the like.

As acid addition salts, may be mentioned inorganic acid addition salts (e.g., hydrochlorides, hydrobromides, sulfates, phosphates, etc.); and organic carboxylic or sulfonic acid addition salts (e.g., formates, acetates, trifluoroacetates, maleates, tartrates, fumarates, methnesulfonates, benzenesulfonates, toluenesulfonates, etc.). Further, may also be mentioned salts with basic or acidic amino acids (e.g., salts with arginine, aspartic acid, glutamic acid, etc.).

The cyclic polypeptide compounds (I) of the present invention also include possible conformers and a pair or more of stereoisomers such as geometric isomers and optical isomers which may exist due to asymmetric carbon atoms.

The preferable ones of the cyclic polypeptide compounds (I) are represented by the following formulas (II) to (VI): (to be continued on the next page)

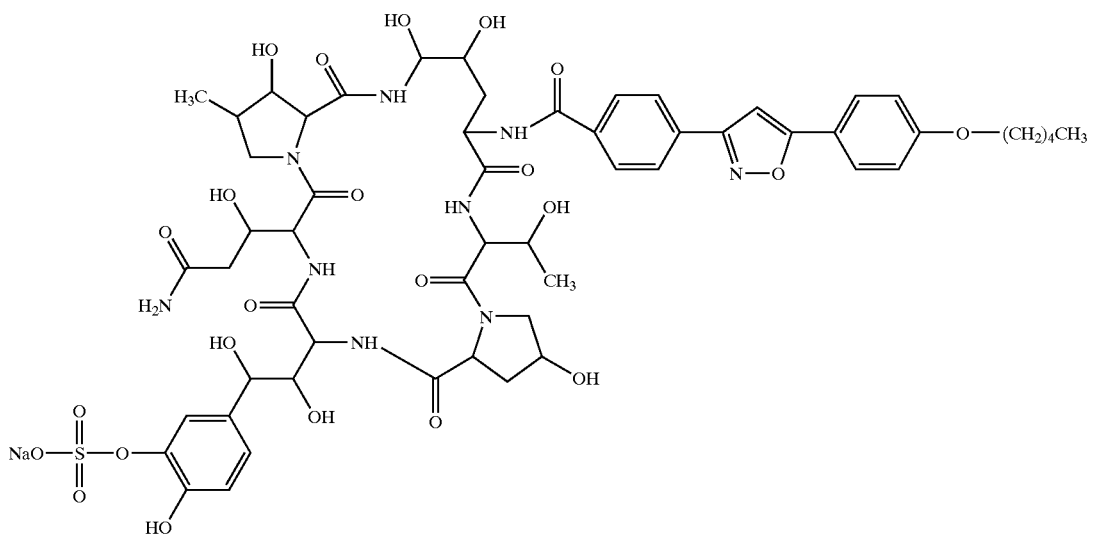

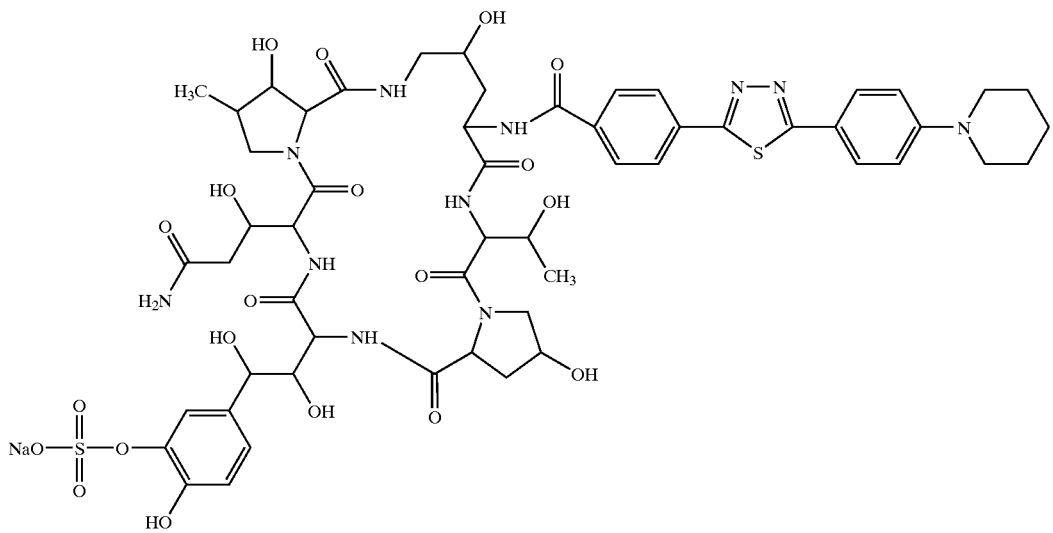

-continued
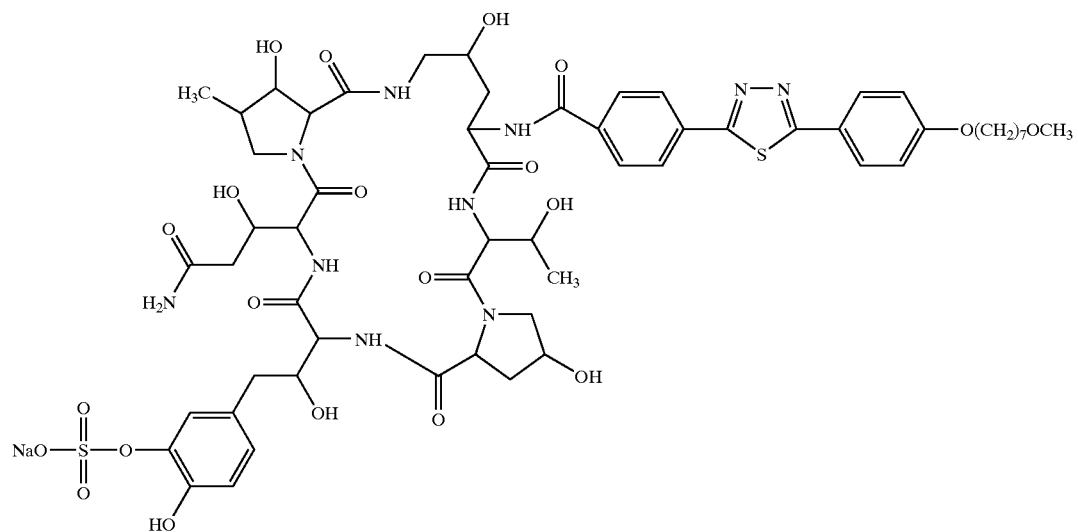
(IV)
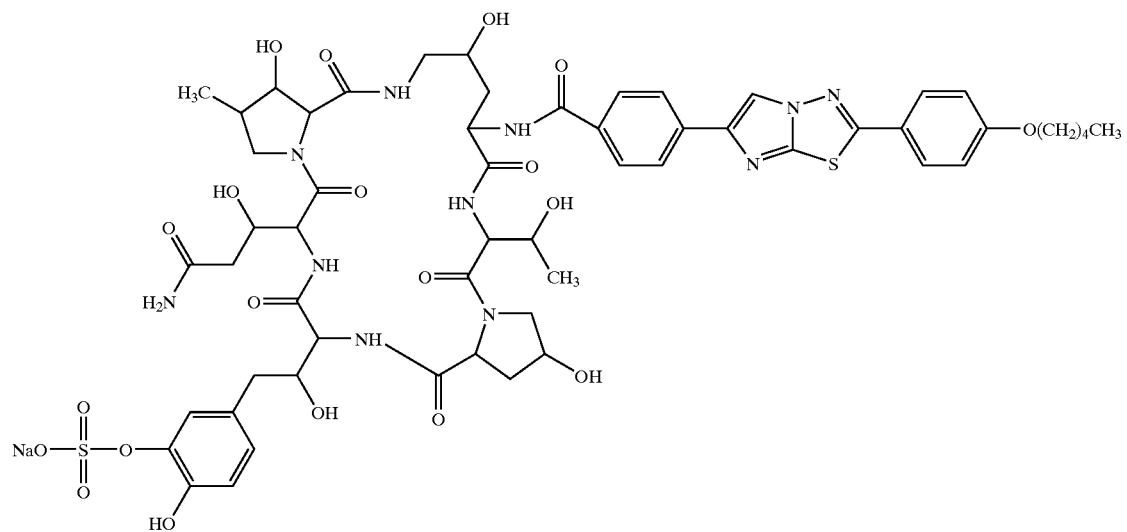
(V)
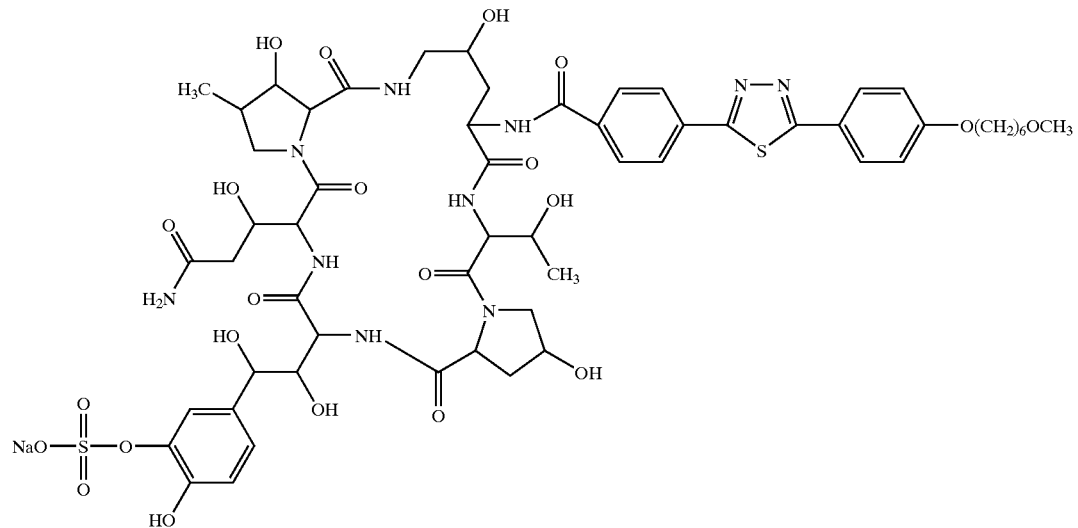
(VI)

The most preferable one is represented by the formula (II).

The amount of the cyclic polypeptide compound (I) or its pharmaceutically acceptable salt contained in the composition for a single unit dosage of the present invention is 0.1 to 400 mg, more preferably 1 to 200 mg, still more preferably 10 to 100 mg, specifically 10, 15, 20, 25, 30, 35, 40, 45, 50, 55, 60, 70, 75, 80, 85, 90, 95 and 100 mg.

As the stabilizer, may be mentioned polysaccharides, disaccharides, sodium chloride and a combination thereof.

Examples of the polysaccharide are dextran, starch, cellulose and hyaluronic acid; and examples of the disaccharide are lactose, maltose and sucrose. The polysaccharide or disaccharide contained in the pharmaceutical composition of the present invention may be α-monohydrate, α-anhydride, β-anhydride or a combination thereof.

The amount of the stabilizer used in the pharmaceutical composition of the present invention should be at least sufficient for stabilizing the cyclic polypeptide compound (I) or its pharmaceutically acceptable salt in the composition. In order to stabilize the cyclic polypeptide compound (I), one part by weight of the stabilizer with respect to one part by weight of the cyclic polypeptide compound (I) or its pharmaceutically acceptable salt in the present composition is sufficient at least. The stabilizer may also serve as a carrier or an excipient. Thus the use amount of stabilizer does not have a particular upper limit and may be determined in consideration of the weight or volume of the composition with respect to a unit dose of the compound and the like. However, such amount is preferably 0.4 to 50 parts by weight, more preferably 0.6 to 20 parts by weight, still more preferably 0.8 to 10 parts by weight with respect to one part by weight of the cyclic polypeptide compound (I) or its pharmaceutically acceptable salt, though it varies depending upon the kind and the used amount of the cyclic polypeptide compound (I) or its pharmaceutically acceptable salt, its preparation form and/or the like. Specifically, it is more preferable that 1 to 20 parts, still more preferably 2 to 10 parts by weight of the disaccharide are used with respect to one part by weight of the cyclic polypeptide compound (I) or its pharmaceutically acceptable salt. Specifically, it is more preferable that 0.6 to 20 parts, still more preferably 0.8 to 10 parts by weight of sodium chloride are used with respect to one part by weight of the cyclic polypeptide compound (I) or its pharmaceutically acceptable salt.

The pharmaceutical composition of the present invention may be produced according to methods known in the art with using additives if necessary. Here, *Basic Lecture on Development of Pharmaceuticals XI* 20 *Production of Pharmaceuticals* (the second volume) (edited by Kyosuke Tsuda and Hisashi Nogami and published by Chizyo Shoten) is mentioned for reference. The lyophilized composition may be obtained by preparing an aqueous solution of the cyclic polypeptide compound (I) or its pharmaceutically acceptable salt and the stabilizer, optionally adding a pH adjustor (citric acid anhydrous, sodium hydroxide, etc.) as required to attain pH 4.0–7.5, preferably pH 4.5–7.0, and then lyophilizing the resulting solution in vial according to a conventional method. Thus, the stabilized pharmaceutical composition in lyophilized form, when dissolved in purified water, preferably gives a solution of pH 4.0 to 7.5, more preferably pH 4.5 to 7.0. It is preferable that the thus prepared composition in lyophilized form is sealed and stored with shading. The lyophilized composition can be loaded in each vial in the solution form before lyophilizing or in lyophilized powder form after lyophilizing.

Since the cyclic polypeptide compound is not satisfactorily stable to humidity, it is necessary that the lyophilized composition of the present invention contains 3.4% by weight or less of water, preferably 3.0%, more preferably 2.0%.

Usually the stabilized pharmaceutical composition in lyophilized form is dissolved in isotonic sodium chloride solution as required and used as an injection solution. The pharmaceutical composition of the present invention may be used as an injection preparation which requires some compounding before use.

BEST MODE FOR CARRYING OUT THE INVENTION

The present invention is now described in further detail by way of examples and test examples, which should not be construed to limit the scope of the invention. In the examples, the compounds of formula (II) to (VI) are referred to as Compounds (II) to (VI), respectively.

EXAMPLE 1

Compound (II) 25 g

Lactose 200 g anhydrous Citric acid in a suitable amount

Sodium hydroxide in a suitable amount

Lactose was dissolved in purified water (2000 ml) under heating below 50° C. After cooling below 20° C., the lactose solution was added with Compound (II) avoiding bubbling under gently stirring. After adding 2% aqueous citric acid solution (9.5 ml), the solution was added with 0.4% aqueous sodium hydroxide solution (about 24 ml) to adjust pH 5.5 followed by diluting with purified water to make a given volume (2500 ml). The resulting solution was dispensed into 1,000 vials of 10 mL volume, 2.5 ml per vial. The solution in the respective vials was lyophilized by using the lyophilizer (RL-603BS manufactured by Kyowa Shinku Co., Ltd) by the conventional method to obtain lyophilized compositions each containing 25 mg of Compound (II).

EXAMPLE 2

Lyophilized compositions each containing 50 mg of Compound (II) were obtained in the same manner as in Example 1 except that the amount of Compound (II) used was 50 g.

EXAMPLE 3

Lyophilized compositions each containing 25 mg of Compound (II) are obtained in the same manner as in Example 1 except that 150 g of maltose is used instead of lactose.

EXAMPLE 4

Lyophilized compositions each containing 50 mg of Compound (II) are obtained in the same manner as in Example 1 except that the amount of Compound (II) used is 50 g instead of 25 g and 250 g of sucrose is used instead of lactose.

EXAMPLE 5

Lyophilized compositions each containing 25 mg of Compound (II) are obtained in the same manner as in Example 1 except that 25 g of sodium chloride is used instead of lactose.

EXAMPLE 6

Lyophilized compositions each containing 10 mg of Compound (II) are obtained in the same manner as in Example 1 except that the amount of Compound (II) used is 10 g instead of 25 g and 100 g of dextran is used instead of lactose.

EXAMPLE 7

Lyophilized compositions each containing 25 mg of Compound (III) are obtained in the same manner as in Example 1 except that 25 g of Compound (III) is used instead of Compound (II) and 200 g of maltose is used instead of lactose.

EXAMPLE 8

Lyophilized compositions each containing 10 mg of Compound (IV) are obtained in the same manner as in Example 1 except that 10 g of Compound (IV) is used instead of Compound (II) and the amount of lactose used is 100 g instead of 200 g.

EXAMPLE 9

Lyophilized compositions each containing 50 mg of Compound (V) are obtained in the same manner as in Example 1 except that 50 g of Compound (V) is used instead of Compound (II) and 50 g of sodium chloride is used instead of lactose.

EXAMPLE 10

Lyophilized compositions each containing 10 mg of Compound (VI) are obtained in the same manner as in Example 1 except that 10 g of Compound (VI) is used instead of Compound (II) and 100 g of dextran is used instead of lactose.

Test Example 1
Effect of Stabilizer in Stabilizing Lyophilized Compositions of Compound (II)

10 mg of Compound (II) and, as a stabilizer, 100 mg of lactose or 9 mg of sodium chloride were dissolved completely in 1 ml of water. The resulting solutions were lyophilized and maintained at 70° C. in glass vials. Nine days after, the resulting compositions were tested on their appearance, the residual amount of Compound (II), and others. As a control, used was a solution of Compound (II) without any stabilizers. The results are shown in Table 1.

TABLE 1

| Stabilizers | Test Items | 0 hours | After 9 days |
|---|---|---|---|
| Control: nil | Appearance | White mass | Slightly yellow mass |
| | pH* | 7.1 | 2.7 |
| | Residual amount (%) | 100.0 | 8.0 |
| | Water content (%) | 1.3 | — |
| Lactose (100 mg) | Appearance | White mass | White mass |
| | pH* | 6.4 | 6.1 |
| | Residual amount (%) | 100.0 | 99.5 |
| | Water content (%) | 1.0 | — |
| Sodium chloride (9 mg) | Appearance | White mass | White mass |
| | pH* | 6.7 | 6.3 |
| | Residual amount (%) | 100.0 | 75.9 |
| | Water content (%) | 0.7 | — |

*pH of reconstituted solutions of compositions in 1 ml of water

Test Example 2

The similar tests were conducted in the same manner as in Test Example 1 except that 100 mg of maltose, 50 mg of sucrose or 50 mg of glucose was used as a stabilizer. The results are shown in Table 2. (to be continued on the next page)

TABLE 2

| Stabilizers | Test Items | 0 hours | After 9 days |
|---|---|---|---|
| Control:nil | Appearance | White mass | White mass |
| | pH* | 6.8 | 5.4 |
| | Residual amount (%) | 100.0 | <75.0 |
| | Water content (%) | 3.3 | — |
| Maltose (100 mg) | Appearance | White mass | White mass |
| | pH* | 7.3 | 6.7 |
| | Residual amount (%) | 100.0 | 98.6 |
| | Water content (%) | 0.9 | — |
| Sucrose (50 mg) | Appearance | White mass | White melt |
| | pH* | 6.9 | 7.0 |
| | Residual amount (%) | 100.0 | 82.4 |
| | Water content (%) | 1.1 | — |
| Glucose (50 mg) | Appearance | White melt | Brown melt |
| | pH* | 6.9 | 3.6 |
| | Residual amount (%) | 100 | 1.1 |
| | Water content (%) | 4.3 | — |

*pH of reconstituted solutions of compositions in 1 ml of water

As is obvious from Tables 1 and 2, the lyophilized composition of Compound (II) and lactose, sodium chloride, maltose or sucrose was significantly stable as compared with the one not containing any stabilizers or containing other stabilizers.

Test Example 3
Dependence of the Stability of Lyophilized Compositions of Compound (II) upon the Amount of Lactose Added Tests were carried out in the same manner as in Test example 1 except that 20 mg, 50 mg, 100 mg or 200 mg of lactose were added as a stabilizer. Table 3 shows the results of tests by observation of the appearance of compositions, the residual amount of Compound (II), the appearance of reconstituted solutions of compositions in 1 ml of water, and the like. Incidentally, it took 15 seconds to reconstitute the compositions in 1 ml of water.

TABLE 3

| Amount of lactose added (mg) | Test Items | 0 hours | After 9 days at 70° C. | After 3 months at 40° C. and a 75% humidity |
|---|---|---|---|---|
| 20 | Appearance | White mass | Slightly yellow mass | White mass |
| | Color* | Colorless | White | Colorless |
| | Clarity* | Clear | Not clear | Clear |
| | pH* | 6.09 | 3.03 | 6.57 |
| | Residual amount (%) | 100.0 | 88.09 | 100.0 |
| | Total impurities (%) | 3.44 | 12.3 | 3.99 |
| | Water content (%) | 1.2 | — | — |
| 50 | Appearance | White mass | White mass | White mass |
| | Color* | Colorless | Colorless | Colorless |
| | Clarity* | Clear | Clear | Clear |
| | pH* | 6.57 | 5.56 | 6.26 |
| | Residual amount (%) | 100.0 | 96.7 | 99.8 |
| | Total impurities (%) | 3.32 | 7.37 | 4.21 |
| | Water content (%) | 0.5 | — | — |
| 100 | Appearance | White mass | White mass | White mass |
| | Color* | Colorless | Colorless | Colorless |
| | Clarity* | Clear | Clear | Clear |
| | pH* | 6.58 | 6.08 | 5.80 |
| | Residual amount (%) | 100.0 | 96.7 | 99.6 |
| | Total impurities (%) | 3.43 | 7.08 | 3.96 |
| | Water content (%) | 0.3 | — | — |

TABLE 3-continued

| Amount of lactose added (mg) | Test Items | 0 hours | After 9 days at 70° C. | After 3 months at 40° C. and a 75% humidity |
|---|---|---|---|---|
| 200 | Appearance | White mass | White mass | White mass |
|  | Color* | Colorless | Colorless | Colorless |
|  | Clarity* | Clear | Clear | Clear |
|  | pH* | 6.78 | 5.70 | 5.36 |
|  | Residual amount (%) | 100.0 | 96.1 | 99.6 |
|  | Total impurities (%) | 3.40 | 7.30 | 4.35 |
|  | Water content (%) | 0.3 | — | — |

*Color, clarity and pH of reconstituted solutions of compositions in 1 ml of water As is obvious from Table 3, the lyophilized compositions of 10 mg of Compound (II) and various amount of lactose had no problem in their stability.

Test Example 4
Stability of Lyophilized Compositions of 200 mg of Lactose and Compound (II) in Vial Tests were carried out in the same manner as in Test Example 1 except that 12.5 mg, 25 mg, 50 mg, 75 mg or 100 mg of Compound (II) were used with 200 mg of lactose. Table 4 shows the results of the tests on the residual amount of Compound (II) in the resulting compositions and the like. Regarding all the compositions, their appearance is a white mass, the time for reconstitutional dissolution was 15 seconds, and the color and the clarity of reconstituted solutions of the compositions were colorless and transparent.

TABLE 4

| Amount of Compound (II) added (mg) | Test Items | 0 hours | After 9 days at 70° C. | After 21 days at 60° C. | After 3 months at 40° C. and a 75% humidity |
|---|---|---|---|---|---|
| 12.5 | pH* | 6.63 | 6.15 | 6.31 | 6.08 |
|  | Residual amount (%) | 100.0 | 98.1 | 97.5 | 99.6 |
|  | Total impurities (%) | 2.24 | 3.95 | 3.75 | 2.71 |
|  | Water content (%) | 1.3 | — | — | — |
| 25 | pH* | 6.37 | 6.07 | 6.11 | 6.14 |
|  | Residual amount (%) | 100.0 | 99.3 | 98.2 | 101.2 |
|  | Total impurities (%) | 2.25 | 4.03 | 3.49 | 2.68 |
|  | Water content (%) | 1.1 | — | — | — |
| 50 | pH* | 6.26 | 5.99 | 6.00 | 6.00 |
|  | Residual amount (%) | 100.0 | 97.9 | 97.3 | 100.5 |
|  | Total impurities (%) | 2.25 | 3.95 | 3.68 | 2.74 |
|  | Water content (%) | 1.2 | — | — | — |
| 75 | pH* | 6.13 | 5.95 | 5.96 | 6.04 |
|  | Residual amount (%) | 100.0 | 98.1 | 97.7 | 99.0 |
|  | Total impurities (%) | 2.28 | 4.14 | 3.83 | 2.76 |
|  | Water content (%) | 0.9 | — | — | — |
| 100 | pH* | 6.03 | 5.92 | 5.88 | 5.85 |
|  | Residual amount (%) | 100.0 | 97.8 | 96.7 | 99.5 |
|  | Total impurities (%) | 2.46 | 4.15 | 3.92 | 2.79 |
|  | Water content (%) | 1.3 | — | — | — |

*pH of reconstituted solutions of compositions in 5 ml purified water

As is obvious from Table 4, all the lyophilized compositions were stable.

Test Example 5
Stability Test

The pharmaceutical compositions obtained in Examples 1 and 2 were stored at room temperature. After 18 months, the residual ratio of Compound (II) was 98% in all the compositions.

Test Example 6
Dependence of the Stability of Lyophilized Compositions of Compound (II) Upon the pH Value of the Solution of the Composition Before Lyophilizing 10 mg of Compound (II) and, as a stabilizer, 100mg of lactose were dissolved completely in 1 ml of citrate-NaOH buffer having different pH value between pH 4.0 to 7.0. The resulting solutions having different pH values were lyophilized and maintained at 70° C. in glass vials. Nine days after, the resulting compositions were tested on their pH and the residual amount of Compound (II). The results are shown in Table 5.

TABLE 5

|  | pH of the solution of the composition before lyophilizing | 4.0 | 4.5 | 5.0 | 5.5 | 6.0 | 6.5 | 7.0 |
|---|---|---|---|---|---|---|---|---|
| 0 hours | pH* | 3.9 | 4.4 | 4.8 | 5.4 | 5.8 | 6.4 | 6.8 |
|  | Water content (%) | 0.2 | 0.2 | 0.3 | 0.3 | 0.3 | 0.4 | 0.3 |
|  | Residual amount (%) |  |  |  | 100 |  |  |  |
| 9 days | pH* | 4.0 | 4.5 | 4.9 | 5.4 | 5.8 | 6.4 | 6.8 |
|  | Residual amount (%) | 94.4 | 95.9 | 97.4 | 98.5 | 97.7 | 96.9 | 95.8 |

*pH of reconstituted solutions of compositions in 5 ml of purified water

As is obvious from the table 5, the pharmaceutical composition of the present invention is stable after lyophilizing the solution containing Compound (II) at pH 4.0 to 7.0 at least, preferably at pH 4.5 to 7.0.

Test Example 7
Dependence of the Stability of Lyophilized Compositions of Compound (II) Upon the Water Content of the Composition 10 mg of Compound (II) and, as a stabilizer, 50 mg of lactose were dissolved completely in 1 ml of water. The resulting solutions were lyophilized and maintained at 70° C. in glass vials. Nine days after, the resulting compositions were tested on their pH, their water content and the residual amount of Compound (II). The results are shown in Table 6.

TABLE 6

| Water content at 0 hours (%) |  | 0.9 | 1.4 | 2.6 | 3.4 | 5.1 |
|---|---|---|---|---|---|---|
| 0 hours | pH* |  |  | 7.1 |  |  |
| After 9 days | pH* | 7.5 | 7.1 | 6.8 | 6.8 | 3.5 |
|  | Water content (%) | 2.5 | 2.9 | 3.6 | 4.3 | 5.4 |
|  | Residual amount (%) | 97.6 | 98.1 | 97.1 | 92.7 | 18.3 |

*pH of reconstituted solutions of compositions in 1 ml of water

As is obvious from Table 6, the pharmaceutical composition of the present invention is stable containing about 3.5%, more particularly 3.4% by weight or less of water.

According to the present invention, provided is a composition in lyophilized form in which the cyclic polypeptide compound (I) or its pharmaceutically acceptable salt are stabilized by a stabilizer such as polysaccharide, disaccharide and sodium chloride.

The mechanism of the stabilization of the cyclic polypeptide compound (I) or its pharmaceutically acceptable salt by the stabilizer such as polysaccharide, disaccharide and sodium chloride is still to be unknown, but it may be that the stabilizer adsorbs water in lyophilized cakes and that the stabilizer serves to disperse the compound or its pharmaceutically acceptable salt uniformly in the composition.

The cyclic polypeptide compound (I) has an antifungal activity, particularly against the following fungi.

Acremonium,
Absidia (e.g., *Absidia corymbifera*, etc);
Aspergillus (e.g., *Aspergillus clavatus, Aspergillus flavus, Aspergillus fumigatus, Aspergillus nidulans, Aspergillus niger, Aspergillus terreus, Aspergillus versicolor*, etc);
Blastomyces (e.g., *Blastomyces dermatitidis*, etc);
Candida (e.g., *Candida albicans, Candida glabrata, Candida guilliermondii Candida kefyr, Candida krusei, Candida parapsilosis, Candida stellatoides, Candida tropicalis, Candida utilis*, etc.);
Cladosporium (e.g., *Cladosporium trichoides*, etc);
Coccidioides (e.g., *Coccidioides immitis*, etc);
Cryptococcus (e.g., *Cryptococcus neoformans*, etc);
Cunninghamella (e.g., *Cunninghamella elegans*, etc);
Dermatophyte;
Exophiala (e.g., *Exophiala dermatitidis, Exophiala spinifera*, etc);
Epidernophyton (e.g., *Epidernophyton floccosum*, etc);
Fonsecaea (e.g., *Fonsecaea pedrosoi*, etc);
Fusarium (e.g., *Fusarium solani*, etc);
Geotrichum (e.g., *Geotrichum candiddum*, etc);
Histoplasma (e.g., *Histoplasma capsulatum* var. *capsulatum*, etc);
Malassezia (e.g., *Malassezia furfur*, etc);
Microsporum (e.g., *Microsporum canis, Microsporum gypseum*, etc);
Mucor;
Paracoccidioides (e.g., *Paracoccidioides brasiliensis*, etc);
Penicillium (e.g., *Penicillium marneffei*, etc);
Phialophora;
Pneumocystis (e.g., *Pneumocystis carinii*, etc);
Pseudallescheria (e.g., *Pseudallescheria boydii*, etc);
Rhizopus (e.g., *Rhizopus microsporus* var. *rhizopodiformis, Rhizopus oryzae*, etc);
Saccharomyces (e.g., *Saccharomyces cerevisiae*, etc);
Scopulariopsis;
Sporothrix (e.g., *Sporothrix schenchii*, etc);
Trichophyton (e.g., *Trichophyton mentagrophytes, Trichophyton rubrum*, etc);
Trichosporon (e.g., *Trichosporon asahii, Trichosporon cutaneum*, etc).

The above fungi are well known to cause various infection diseases in skin, hair, nail, oral mucosa, gastrointestinal tract, bronchus, lung, endocardium, brain, meninges, urinary organ, vaginal protion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, and so on.

Therefore, the cyclic polypeptide compound (I) of the present composition is useful for preventing and treating various infectious diseases, such as dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and so on.

A commercial package comprising the cyclic polypeptide compound (I) of the present composition and a written matter associated therewith, wherein the written matter states that the pharmaceutical composition can or should be used for preventing or treating infections disease.

What is claimed is:

1. A stabilized pharmaceutical composition in lyophilized form which comprises:
a cyclic polypeptide compound of the formula (I):

(I)

or its pharmaceutically acceptable salt, and
lactose.

2. The composition according to claim 1 which contains 0.4 to 50 parts by weight of lactose with respect to one part by weight of the cyclic polypeptide compound or its pharmaceutically acceptable salt.

3. The composition according to claim 1 which contains 0.1 to 400 mg of the cyclic polypeptide compound or its pharmaceutically acceptable salt in a single unit dose.

4. The composition according to claim 1 prepared by:
dissolving the cyclic polypeptide compound (I) or its pharmaceutically acceptable salt, lactose and optionally a pH adjustor in a purified water and
lyophilizing the solution.

5. The composition of claim 1 which, when dissolved in purified water, gives a solution of pH 4.0 to 7.0.

6. The composition of claim 1 containing 3.4% by weight or less of water.

7. An injection preparation prepared by dissolving the composition of claim 1 in isotonic sodium chloride solution.

8. A commercial package comprising
the pharmaceutical composition of claim 1 and
a written matter associated therewith,
wherein the written matter states that the pharmaceutical composition can or should be used for treating an infection or a disease.

9. A method for stabilizing a compound of general formula (I) comprising:
mixing said compound with lactose, wherein the compound of general formula (I) is:

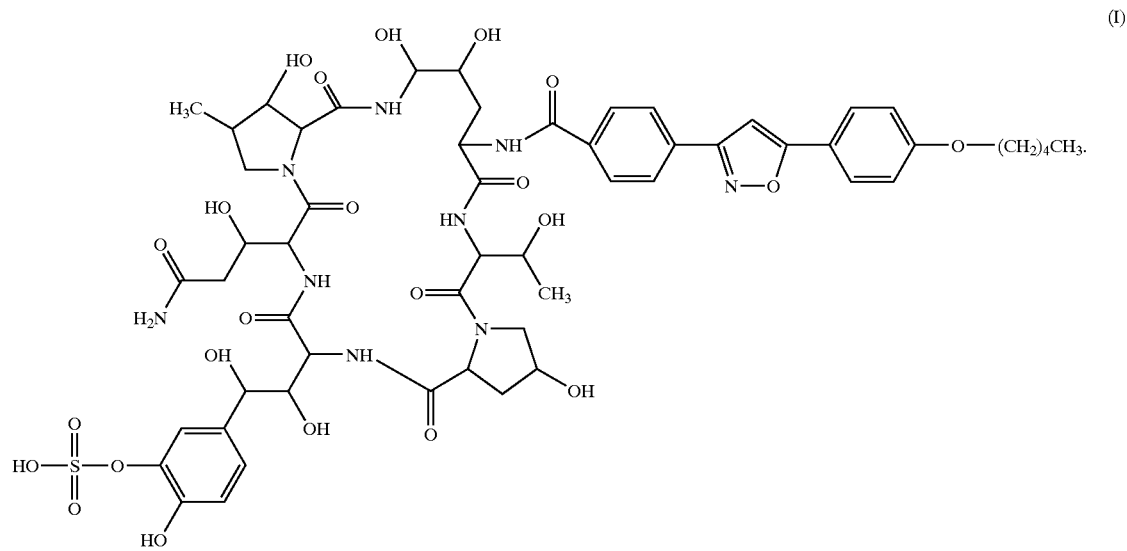

10. The composition according to claim 1, further comprising a pH adjuster.

11. The composition of claim 10, wherein the pH adjuster is acidic.

12. The composition of claim 11, wherein the pH adjuster is basic.

13. A composition comprising the composition of claim 1 and water.

14. The composition of claim 13, wherein the water is present in an isotonic aqueous solution of sodium chloride.

15. The composition of claim 13, wherein the water consisting essentially of purified water.

16. A method for treating a fungal disease comprising administering an effective amount of the composition of claim 13 to a subject in need thereof.

17. The method of claim 16, wherein said compound is administered by injection.

18. The method of claim 16, wherein said disease is selected from the group consisting of dermatophytosis, pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis.

19. A method for treating pneumocystosis comprising administering to a subject in need thereof the compound of claim 13 in an amount effective for treating pneumocystosis.

* * * * *

UNITED STATES PATENT AND TRADEMARK OFFICE
CERTIFICATE OF CORRECTION

PATENT NO. : 6,774,104 B1　　　　　　　　　　　　　　　　　　　　　Page 1 of 1
DATED : August 10, 2004
INVENTOR(S) : Seiji Sawai et al.

It is certified that error appears in the above-identified patent and that said Letters Patent is hereby corrected as shown below:

<u>Title page,</u>
Item [75], Inventors, "Kazumi Otomo," should read -- Kazumi Ohtomo --;

<u>Column 12,</u>
Line 1, delete "(to be continued on the next"
Line 2, delete "page)";

<u>Column 15,</u>
Line 51, "tion diseases in skin," should read -- tions or diseases in skin, --;

<u>Column 16,</u>
Line 5, "treating infections disease." should read -- treating infections or diseases. --;

<u>Column 18,</u>
Line 38, "the compound of" should read -- the composition of --;

Signed and Sealed this

Twenty-eighth Day of December, 2004

JON W. DUDAS
*Director of the United States Patent and Trademark Office*